US007691345B2

(12) United States Patent
Ono

(10) Patent No.: US 7,691,345 B2
(45) Date of Patent: Apr. 6, 2010

(54) STERILIZING AND DISINFECTING APPARATUS

(75) Inventor: Mototsugu Ono, Nara (JP)

(73) Assignee: Shinko Sangyo Co. Ltd., Kobe (JP)

( * ) Notice: Subject to any disclaimer, the term of this patent is extended or adjusted under 35 U.S.C. 154(b) by 1584 days.

(21) Appl. No.: 10/659,259

(22) Filed: Sep. 11, 2003

(65) Prior Publication Data

US 2004/0050877 A1 Mar. 18, 2004

(30) Foreign Application Priority Data

Sep. 13, 2002 (JP) ............................ 2002-268928

(51) Int. Cl.
*A61L 2/20* (2006.01)

(52) U.S. Cl. .................................... 422/292; 134/102.2

(58) Field of Classification Search ................. 422/292; 510/704; 134/102.2
See application file for complete search history.

(56) References Cited

U.S. PATENT DOCUMENTS

| | | | | | |
|---|---|---|---|---|---|
| 1,644,338 | A | * | 10/1927 | Jones | 62/603 |
| 2,191,553 | A | * | 2/1940 | Baier | 514/64 |
| 2,310,633 | A | * | 2/1943 | Heimburger | 239/335 |
| 2,657,166 | A | * | 10/1953 | Stonecipher | 514/511 |
| 2,750,071 | A | * | 6/1956 | Ritchie | 222/3 |
| 2,808,080 | A | * | 10/1957 | Dion-Biro | 141/19 |
| 3,469,788 | A | * | 9/1969 | Glaros | 239/307 |
| 3,977,602 | A | * | 8/1976 | Kirch | 239/74 |
| 6,003,787 | A | * | 12/1999 | Fisher | 239/373 |
| 6,043,287 | A | | 3/2000 | Nakamura | |

FOREIGN PATENT DOCUMENTS

| | | | |
|---|---|---|---|
| JP | 06-024760 | U | 4/1994 |
| JP | 6-84287 | | 10/1994 |
| JP | 2000-237288 | | 9/2000 |

* cited by examiner

*Primary Examiner*—Sean E Conley
(74) *Attorney, Agent, or Firm*—Orum & Roth LLC

(57) ABSTRACT

An apparatus for sterilizing and disinfecting a target space by spraying a chemical including alcohol includes a spray gun 4 to which a chemical container 7 containing a sterilizing and disinfecting chemical including alcohol is attachable, a gas cylinder 1 filled with a compressed carrier gas that does not react with alcohol, and a pressure reducing valve 2 for decompressing the carrier gas discharged in a vaporized state from the gas cylinder 1 to a predetermined pressure, and is constructed so that the pressure reducing valve 2 and the spray gun 4 are directly connected with a gas hose 3 and mounted on a common truck 5. The sterilizing and disinfecting apparatus can operate with a simple structure requiring no power supply, and is much lighter in weight compared to conventional apparatuses.

5 Claims, 4 Drawing Sheets

STERILIZING AND DISINFECTING APPARATUS

This nonprovisional application claims priority under 35 U.S.C. § 119(a) on Patent Application No. 2002-268928 filed in Japan on Sep. 13, 2002, which is herein incorporated by reference.

BACKGROUND OF THE INVENTION

1. Field of the Invention

The present invention relates to a sterilizing and disinfecting apparatus for use in sterilizing and disinfecting a target space by spraying a sterilizing and disinfecting chemical including high-concentration alcohol into the target space.

2. Description of Related Art

As one example of a method of efficiently sterilizing and disinfecting spaces where high cleanliness is required, such as clean rooms of pharmaceutical companies, food factories, wards of hospitals, the inside of ambulances and kitchens of food shops, for example, Japanese Examined Patent Application Laid-Open No. 6-84287 (1994) and Japanese Unexamined Patent Application Laid-Open No. 2000-237288 propose methods in which a sterilizing and disinfecting chemical including alcohol as a main component is sprayed in the form of fine particles.

These methods use a spray gun which is widely used for various painting operations. A chemical tank containing the above-mentioned chemical is attached to the spray gun, and a gas cylinder containing a carrier gas for spraying is connected to the spray gun. The carrier gas supplied from the gas cylinder is injected from the end nozzle of the spray gun, and the chemical in the chemical tank is sucked by a function of the negative pressure created at this time and is sprayed together with the carrier gas.

At this time, by using a carrier gas that does not react with alcohol, such as carbon dioxide gas and nitrogen gas, so as to isolate the sprayed alcohol from oxygen in the space, a high sterilizing and disinfecting function of alcohol can be obtained while avoiding the risk of ignition immediately after spraying. Moreover, by setting an injecting pressure of the carrier gas to control the particle size of the sprayed chemical, it is possible to optimize the settling velocity of the chemical particles in the sprayed space. It is therefore possible to spread the chemical particles throughout the target space including the corners of the space by short-time spraying, and to evenly and satisfactorily sterilize and disinfect the target space. Furthermore, since the sprayed chemical in the form of fine particles includes high-concentration alcohol with quick dry characteristics as a main component, the chemical will evaporate rapidly after adhering to the wall surface, floor surface and the like in the target space without remaining for a long time, and thus there is no need to perform a post treatment including wiping.

On the other hand, when spraying a chemical including alcohol, care must be taken so that the concentration of alcohol in the sprayed space does not exceed the explosion limit. According to the above-described method, however, since the sprayed chemical diffuses evenly throughout the target space, it is possible to achieve the object under a sufficiently low concentration than the explosion limit. Moreover, even in the periphery of the end nozzle of the spray gun, it is possible to maintain an appropriate mixed ratio of the chemical and the carrier gas, and to realize a sprayed condition in which the chemical particles are covered with the carrier gas, by optimizing the design of the end nozzle. It is therefore possible to completely eliminate the risk of explosion, and perform the sterilizing and disinfecting operation without taking into account the presence or absence of fire in the target space.

As described above, the sterilizing and disinfecting methods disclosed in Japanese Examined Patent Application Laid-Open No. 6-84287 (1994) and Japanese Unexamined Patent Application Laid-Open No. 2000-237288 are excellent methods capable of sterilizing and disinfecting any target space in a highly efficient and satisfactory manner. However, these methods use a liquefied gas cylinder filled with carbon dioxide gas or nitrogen gas in a liquefied state as the gas source of carbon dioxide gas or nitrogen gas that serves as a carrier gas, and the liquefied gas supplied from the liquefied gas cylinder is heated and vaporized by a heater and then decompressed to a required injecting pressure to obtain a desired carrier gas. These methods have the following problems.

First, heating with the heater is performed so as to prevent the peripheral part from freezing due to a decrease in temperature caused by volume expansion resulting from the decompression afterward. For this purpose, it is necessary to have the heater and control means for controlling the temperature of the heater and also an anti-freezing mechanism, such as a fin for absorbing heat from outside air in the periphery of the decompression section, and consequently the configuration of the apparatus is complicated.

Second, it is essential to secure a power supply for supplying power to the heater, and thus the place where the apparatus can be used is limited. Besides, if the apparatus comprises an internal power supply, the configuration of the apparatus is further complicated.

Third, a liquefied gas cylinder designed to supply a liquefied gas, i.e., a so-called siphon type liquefied gas cylinder, is originally manufactured to utilize low temperatures of the liquefied gas, and is commercially sold as a large cylinder with a content capacity of 10 Kg or more and a total weight of 20 Kg or more. It is difficult to move a conventional sterilizing and disinfecting apparatus using such a liquefied gas cylinder, even when the apparatus is mounted on a transport truck. Therefore, for example, when sterilizing and disinfecting a plurality of wards of a hospital or the inside of a plurality of ambulances, hard work is required to move the sterilizing and disinfecting apparatus to the respective locations.

BRIEF SUMMARY OF THE INVENTION

The present invention has been made with the aim of solving the above problems, and it is an object of the present invention to provide an apparatus for sterilizing and disinfecting a target space by spraying a chemical including alcohol, which can operate with a simple structure requiring no power supply and is significantly lighter in weight than conventional apparatuses.

A sterilizing and disinfecting apparatus of the present invention supplies a carrier gas that does not react with alcohol to a spray gun to which a chemical container containing a sterilizing and disinfecting chemical including the alcohol is attached, and sprays the chemical into a target space by the function of the carrier gas injected from the end nozzle of the spray gun. This sterilizing and disinfecting apparatus is characterized by comprising: a gas cylinder filled with the compressed carrier gas; a pressure reducing valve, attached near an outlet of the gas cylinder, for decompressing the gas discharged from the outlet to a predetermined pressure; and a gas hose directly connected to the pressure reducing valve and the spray gun.

According to the present invention, a gas cylinder filled with a compressed carrier gas is used. The carrier gas discharged in a vaporized state from the gas cylinder is decompressed by the pressure reducing valve without heating, fed to the spray gun through the gas hose and injected from the end nozzle, so that the chemical in the chemical container attached to the spray gun is sprayed by the function of the injected gas. Such spraying can be realized by optimally designing the gas pressure and flow rate on the outlet side of the decompressing valve, the gas hose, the spray gun and the end nozzle. Thus, it is possible to achieve a light-weight apparatus by a decrease in the weight of the gas cylinder; simplify the configuration of the apparatus by the omission of a heater for heating and temperature control means; and achieve improved handling by the elimination of the necessity of securing a power supply. Besides, the apparatus can be used in any place.

Moreover, in the sterilizing and disinfecting apparatus of the present invention, the gas cylinder, pressure reducing valve and gas hose may be mounted on a common truck shared by the spray gun and chemical container.

According to the present invention, since the light-weight gas cylinder, the pressure reducing valve and the gas hose are mounted on the truck together with the spray gun and the chemical container, it is possible to move the apparatus easily between places of use, thereby achieving improved handling.

Furthermore, in the sterilizing and disinfecting apparatus of the present invention, the chemical container may be detachably attached to the spray gun.

According to the present invention, the chemical container is detachably attached to the spray gun, so that replacement or supply of chemical is easily and safely performed by replacing the container as a unit.

The above and further objects and features of the invention will more fully be apparent from the following detailed description with accompanying drawings.

DETAILED DESCRIPTION OF THE INVENTION

Figure 1:
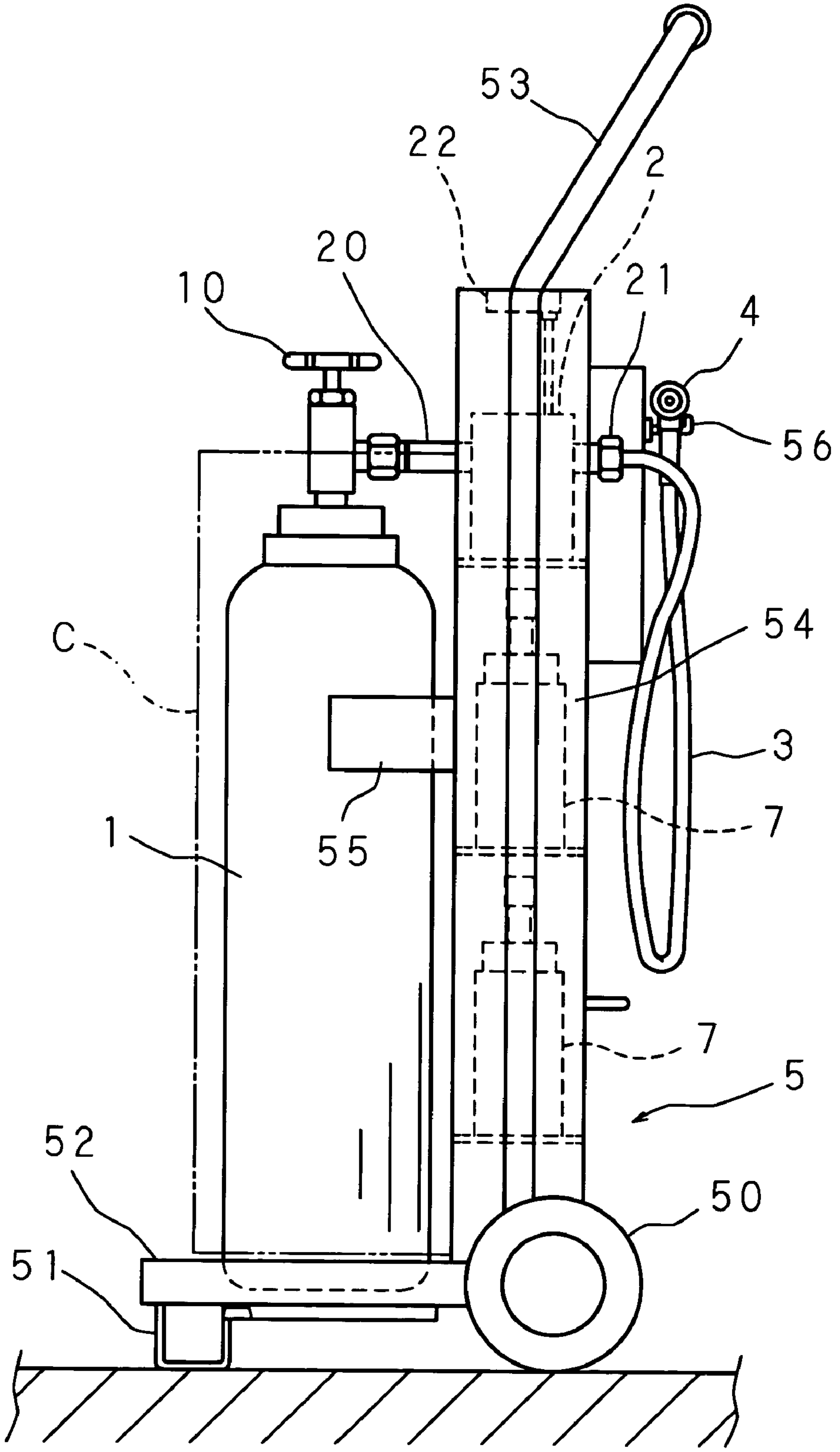
FIG. 1 is a side view showing the entire configuration of a sterilizing and disinfecting apparatus of the present invention.

The following description will explain in detail the present invention, based on the drawings illustrating an embodiment thereof. FIG. 1 is a side view showing the entire configuration of a sterilizing and disinfecting apparatus of the present invention, and FIG. 2 is a plan view of the apparatus seen from above.

Figure 2:
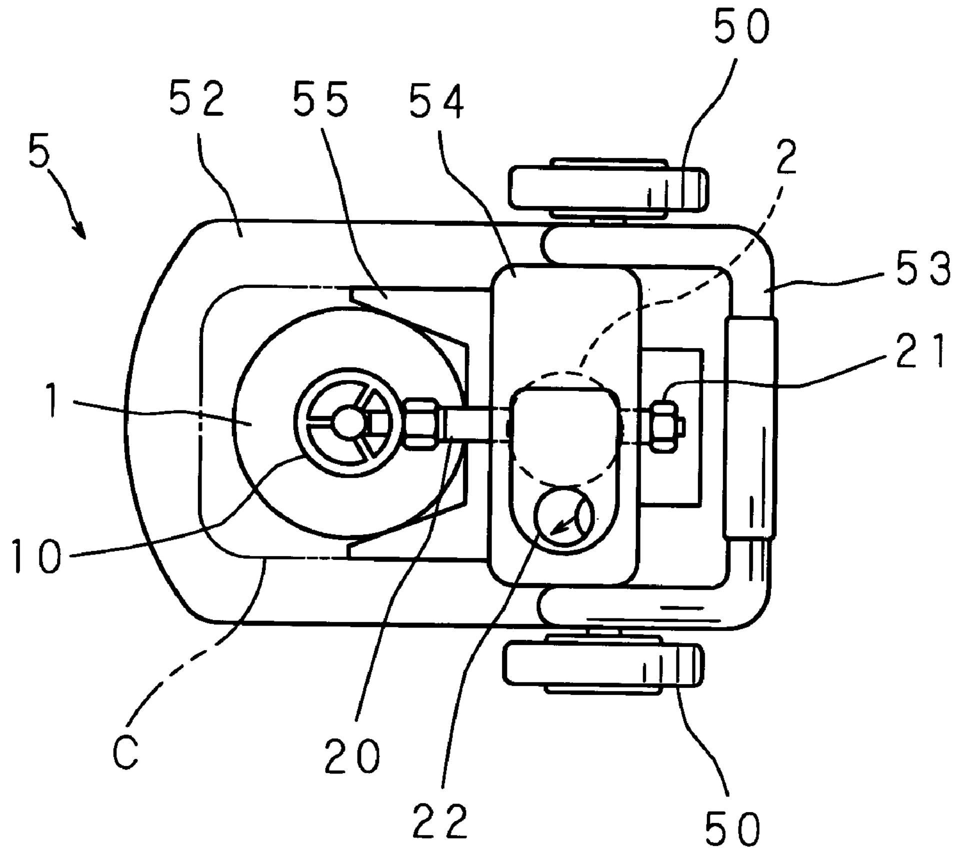
FIG. 2 is a plan view showing the entire configuration of the sterilizing and disinfecting apparatus of the present invention.

As shown in FIGS. 1 and 2, the sterilizing and disinfecting apparatus of the present invention comprises a gas cylinder 1 filled with a compressed carrier gas; a pressure reducing valve 2 connected through a joint 20 to an outlet formed in the upper end of the gas cylinder 1; a gas hose 3 connected through a joint 21 to the discharge side of the pressure reducing valve 2; and a spray gun 4 attached to the other end of the gas hose 3. The gas cylinder 1, pressure reducing valve 2, gas hose 3, and spray gun 4 are mounted on a truck 5 which is movably supported by a pair of right and left wheels 50 (only one side is illustrated).

The truck 5 comprises a pedestal 52 having the right and left wheels 50 attached to the lower portion on one side thereof and a supporting leg 51 protruding from the lower portion on the other side. On the top face of the pedestal 52 supported in parallel to the floor surface as shown in FIG. 1 by the wheels 50 and the supporting leg 51, a grip pipe 53 that has a suitable length and can be stretched upward is mounted at a position above the wheels 50. A supporting box 54 is mounted between the legs of this grip pipe 53.

The gas cylinder 1 is mounted at the center of the above-described pedestal 52, and fixed in an upright position as shown in FIG. 1 by supporting a middle portion in a height direction with a projecting supporter 55 positioned on the same side of the supporting box 54. As shown in FIG. 2, the supporter 55 comprises a recessed portion capable of accepting the trunk portion of the gas cylinder 1, and the gas cylinder 1 accepted in this recessed portion is fixed while maintaining a stable posture by being supported at three points on the circumferential surface of the trunk portion.

Note that it may be possible to place a belt (not illustrated) between the tops on both sides of the supporter 55, to securely fix the gas cylinder 1 by tightening the belt. Moreover, in order to protect the gas cylinder 1 from a colliding object and improve the appearance, it is preferred to cover the outside of the thus fixed gas cylinder 1 with a box-shaped cover C as shown by the two dotted dash rule in FIGS. 1 and 2.

The inside of the gas cylinder 1 is filled with a carrier gas, such as carbon dioxide gas and nitrogen gas, compressed under a predetermined pressure. The carrier gas is discharged in a vaporized state from an outlet that is formed in the upper end of the gas cylinder 1 and can be opened and closed by a valve 10. If carbon dioxide is used as the carrier gas, most of carbon dioxide is in a liquefied state inside the gas cylinder 1, and a vaporized gas residing in the upper part of the gas cylinder 1 is discharged from the outlet. If the nitrogen gas is used as the carrier gas, it is not liquefied by the compression under the above-mentioned pressure, is in a vaporized state even in the gas cylinder 1, and is discharged as it is from the outlet.

As the carrier gas, any gas that does not react with alcohol included in a later-described chemical 8 used for sterilization and disinfection can be employed, and it is possible to use an inert gas such as neon gas and argon gas as well as the above-mentioned carbon dioxide gas and nitrogen gas. However, since the gas will remain in the air after spraying, it is preferred to use carbon dioxide gas or nitrogen gas which is widely present in the air. Besides, the carbon dioxide gas and the nitrogen gas have the advantages of low costs.

As shown by the broken line in FIG. 1, the pressure reducing valve 2 is fixed and supported in a chamber formed in the upper part of the supporting box 54, and the joints 20 and 21 connected to the inlet side and the outlet side of the pressure reducing valve 2 protrude from both side surfaces of the supporting box 54. The outlet formed in the upper end of the gas cylinder 1 is connected to the inlet-side joint 20.

Further, one end of the gas hose 3 having flexibility is connected to an outlet-side joint 21 protruding from the other face of the supporting box 54. Connected to the other end of the gas hose 3 is the spray gun 4 which is to be described later. A gun hook 56 is attached to the upper part of the other face of the supporting box 54, and the spray gun 4 in a non-use state is kept while being caught with the gun hook 56 as shown in FIG. 1. Note that, in FIG. 2, illustration of the gas hose 3 and spray gun 4 is omitted.

The pressure reducing valve 2 is a known valve performing the function of decompressing high-pressure gas fed from the inlet side to a predetermined pressure and feeding it to the outlet side. The pressure reducing valve 2 according to this embodiment is designed to decompress the carrier gas fed from the gas cylinder 1 to a fixed pressure of around 0.2 to 0.5 Mpa and feed it into the gas hose 3 and the spray gun 4. A pressure gauge 22 for detecting the pressure on the outlet side of the pressure reducing valve 2 is mounted on the top surface of the supporting box 54 so that it can be seen from above as shown in FIG. 2.

Figure 3:
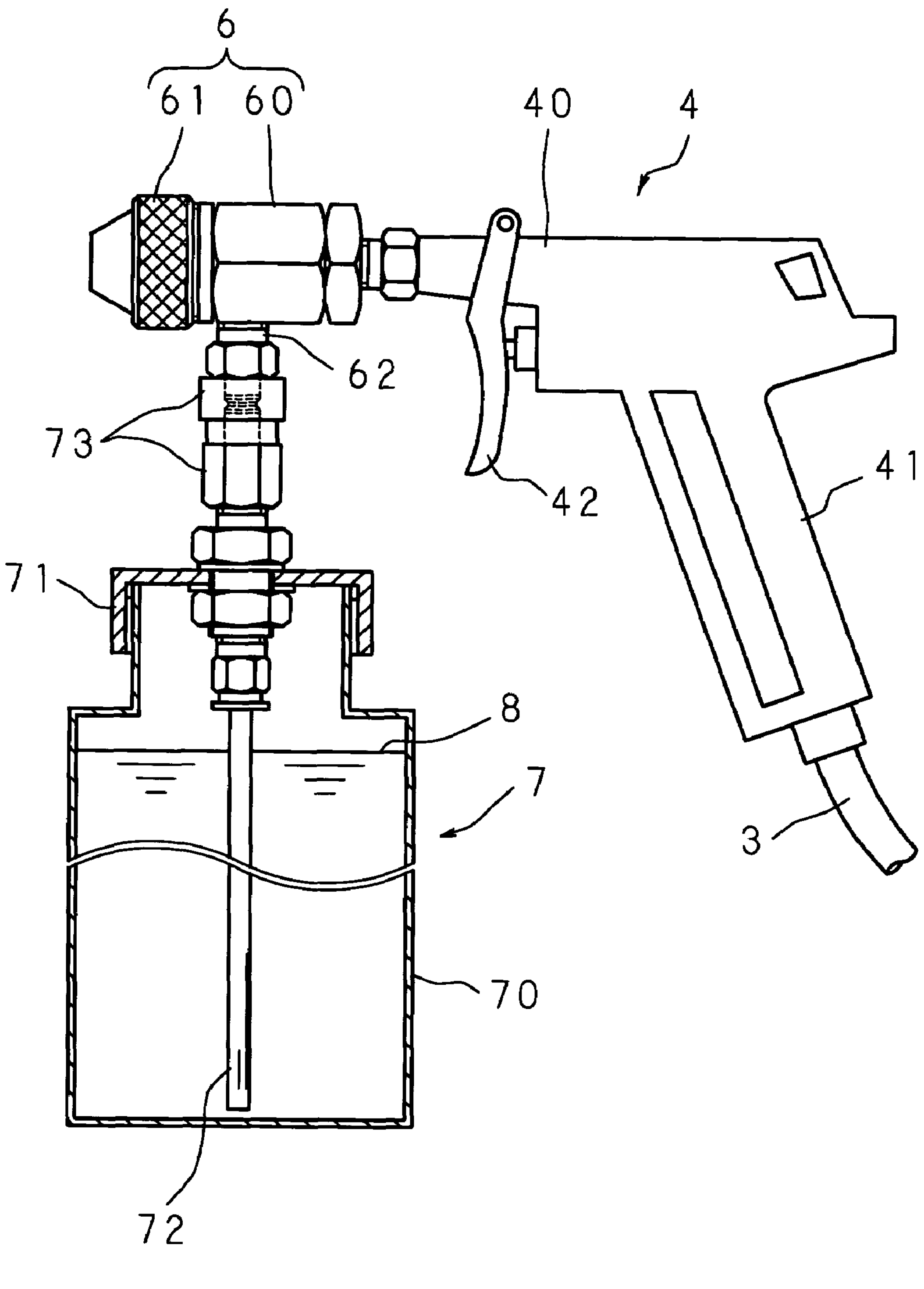
FIG. 3 is a side view showing the structure of a spray gun.

FIG. 3 is a side view showing the structure of the spray gun 4. The spray gun 4 comprises a barrel portion 40, a grip portion 41 and a trigger 42, and has a known structure in which the gas supplied from the gas hose 3 connected to the end of the grip portion 41 is supplied from the front end of the barrel portion 40 by operating the trigger 42. A spray nozzle 6 is attached to the front end of the barrel portion 40.

The spray nozzle 6 comprises a nozzle body 60 in the form of a cylinder with a hexagonal cross section, and a nozzle head 61 fixed to the front end of the nozzle body 60. A communication pipe 62 is connected to the circumferential surface of the nozzle body 60 at the middle part in a direction substantially orthogonal to the nozzle body 60, and a chemical container 7 is attached to the front end of the communication pipe 62.

As shown by the cross section in FIG. 3, the chemical container 7 comprises a container body 70 in the shape of a bottle having an opening on one side, a cover plate 71 for covering the opening of the container body 70 by being screwed on the circumferential edge, and a siphon 72 that passes in and out through the cover plate 71 at the center and is extended to the vicinity of the bottom face of the container body 70. The chemical container 7 is detachably attached to the communication pipe 62 with a coupler 73 attached to the end of the communication pipe 62 and the outside end of the siphon 72.

A sterilizing and disinfecting chemical 8 is contained in such a chemical container 7. The chemical 8, for example, has a composition prepared by mixing a solution including alcohol as a main component with a suitable amount of water-soluble sterilizing and disinfecting agent for improving the sterilization and disinfection effects so that the alcohol concentration is between 65 to 80% by volume. The sterilizing and disinfecting agent to be mixed can be suitably selected depending on the bacterial species subjected to sterilization. Since the sterilizing and disinfecting agent is water soluble, it is well mixed with alcohol as the main component.

Note that, as the alcohol to be included in the chemical 8, it is possible to use alcohol having high volatility and high sterilization and disinfection effects, such as ethyl alcohol, methyl alcohol and isopropyl alcohol. It is also possible to suitably mix these alcohols, or use a denatured alcohol obtained by mixing a predetermined denaturant (perfume or the like). The alcohol to be used may be selected by taking into account the safety and cost in addition to the above-mentioned volatility and sterilization and disinfection effects.

The chemical container 7 containing such a chemical 8 can be easily attached and detached with the use of the coupler 73. It is possible to prepare a plurality of chemical containers containing the above-mentioned different types of sterilizing and disinfecting agents and suitably replace them according to the target space or target bacterial species. Note that it is also possible to use a single chemical container 7 by opening the cover plate 71 and supplying or replacing the chemical 8 in the chemical container 7 as occasion arises. In the case of using a plurality of chemical containers 7, as shown in FIG. 1, it is possible to provide, in the supporting box 54 on the truck 5*a*, a storage room for storing the chemical containers 7 before or after use, thereby enabling highly efficient sterilizing and disinfecting operations against a plurality of types of bacteria in a plurality of places.

Figure 4:
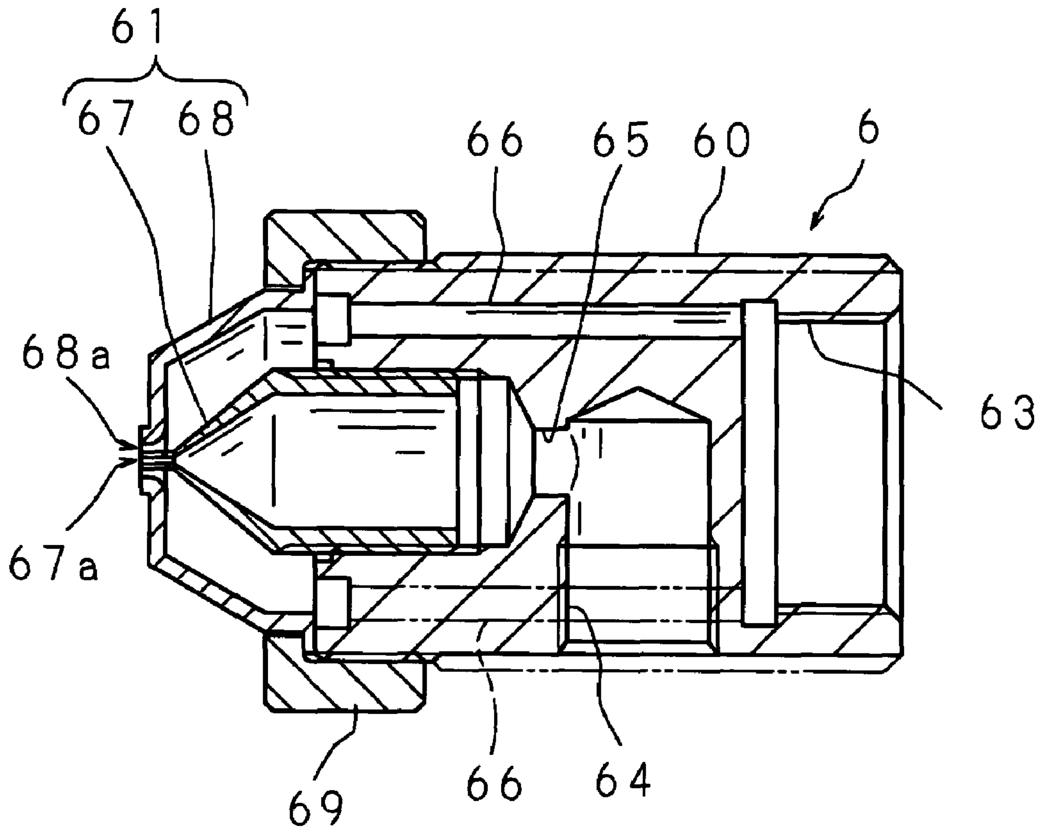
FIG. 4 is a vertical cross-sectional view of a spray nozzle.

FIG. 4 is a vertical cross-sectional view of the spray nozzle 6. As shown in FIG. 4, a connecting pore 63 for connecting the spray gun 4 is formed in the axial center portion of one end face of the nozzle body 60, and a coupling pore 64 for connecting the communication pipe 62 is formed in the outer circumferential surface of the middle portion of the nozzle body 60. The coupling pore 64 communicates with the other end face of the nozzle body 60 to which the nozzle head 61 is attached, through a chemical passage 65 formed in the axial center portion of the nozzle body 60. The connecting pore 63 communicates with said other end face of the nozzle body 60 through a plurality of gas passages 66 formed at equal intervals outside the chemical passage 65.

The nozzle head 61 comprises an inner nozzle 67 screwed into and fixed at a screw hole formed in an end of the chemical passage 65, and an outer nozzle 68 surrounding the outside of the inner nozzle 67. The outer nozzle 68 is fixed by sandwiching a stopper portion provided on the circumference thereof between the end face of the nozzle body 60 and a stopper ring 69 fastened to the outer circumference of the nozzle body 60 on the same side. Each of the inner nozzle 67 and outer nozzle 68 has a shape with a diameter narrowing toward the tip thereof like a funnel. A liquid jet orifice 67*a* of a small diameter is formed in the tip of the inner nozzle 67, and an annular gas jet orifice 68*a* is formed in the tip of the outer nozzle 68 so that it is located between the outer nozzle 68 and the liquid jet orifice 67*a*. The chemical passage 65 communicates with the inside of the inner nozzle 67. The gas passages 66 communicate with an annular space between the outer nozzle 68 and the inner nozzle 67.

The sterilizing and disinfecting apparatus of the present invention constructed as described above is used by opening the valve 10 in the upper end of the gas cylinder 1, holding the spray gun 4 with the tip of the spray nozzle 6 directed into a target space, and pulling the trigger 42 of the spray gun 4. Thus, after the carrier gas inside the gas cylinder 1 is decompressed to a predetermined pressure by the pressure reducing valve 2, it is fed to the spray nozzle 6 through the gas hose 3 and the spray gun 4, introduced into the outer nozzle 68 through the gas passages 66 formed in the nozzle body 60, and jetted out from the gas jet orifice 68*a* formed in the tip of the outer nozzle 68.

In the process of injecting the carrier gas as described above, there is a possibility that volume expansion due to decompression in the pressure reducing valve 2 causes the peripheral part to freeze. However, it is possible to delay the time to freeze by appropriately determining the feed rate of the carrier gas.

The carrier gas feed rate is determined by the pressure on the outlet side of the pressure reducing valve 2 that is set as described above and the strength of the internal resistance of the gas passage on the outlet side of the pressure reducing valve 2, namely, the gas hose 3, spray gun 4 and spray nozzle 6, whereas the necessary continuous injection time of the carrier gas under the condition of use to be described later is around several minutes, except for an excessively large target space. By appropriately designing the gas hose 3, spray gun 4 and spray nozzle 6, the continuous injection for such a period of time can be realized without causing freezing. It was confirmed by experiments that continuous injection for 15 minutes or more is possible by optimally designing the gas hose 3, spray gun 4 and spray nozzle 6.

A negative pressure is created around the liquid jet orifice 67*a* in the tip of the inner nozzle 67 by the injection of the carrier gas as described above, and the inside of the inner nozzle 67, the chemical passage 65, the coupling pore 64, and the inside of the communication pipe 62 have negative pressure. As a result, the chemical 8 in the chemical container 7 connected to the communication pipe 62 is sucked into the siphon 72, reaches the inside of the inner nozzle 67 through the coupling pore 64 and the chemical passage 65, is jetted out from the liquid jet orifice 67*a* opened in the tip of the inner nozzle 67, and sprayed as small diameter particles by the function of the carrier gas injected from the gas jet orifice 68*a*.

The particle size of the chemical 8 sprayed in this manner is determined by the design of the nozzle head 61, particularly the sizes of the gas jet orifice 68*a* and liquid jet orifice 67*a*. In the sterilizing and disinfecting apparatus of the present invention, the nozzle head 61 is designed so that the particle size is between 15 and 20 μm under the above-mentioned conditions of the pressure and volume of carrier gas.

In the sterilizing and disinfecting apparatus of the present invention, as the gas source of a carrier gas, a gas cylinder 1 filled with the compressed gas is used. As this type of gas cylinder 1, gas cylinders with various content capacities such as 1 Kg, 3 Kg and 5 Kg are commercially available, and even a relatively large gas cylinder 1 with a content capacity of 5 Kg has a total weight of 24 Kg or so. Besides, the carrier gas fed from the gas cylinder 1 is designed to be delivered to the spray gun 4 without heating and injected from the spray nozzle 6, and therefore it is not necessary to use heater for heating and temperature control means for the heater.

The chemical 8 sprayed with such a particle size is widely spread throughout the target space, drifts while gradually settling, and then adheres to the inside surface (floor surface, wall surface, etc.) in the target space. During this time, the target space is sterilized and disinfected by the functions of the alcohol as the main component and the added water-soluble sterilizing and disinfecting agent. At this time, since the carrier gas that does not react with alcohol, such as carbon dioxide gas and nitrogen gas, is used, it is possible to isolate the alcohol in the chemical 8 sprayed from the spray nozzle 6 from oxygen in the target space, thereby obtaining a high sterilizing and disinfecting function of alcohol while avoiding the risk of ignition immediately after spraying. Moreover, since the sprayed chemical 8 in the form of fine particles includes high-concentration alcohol with quick dry characteristics as the main component, it rapidly evaporates after adhering to the inside surface in the target space without residing for a long time. Thus, there is no possibility of new breeding of various types of bacteria by the remaining moisture, and a post treatment including wiping is unnecessary.

Therefore, even when a relatively large carbon dioxide gas cylinder having a content capacity of 5 Kg is used, the total weight of the apparatus including the pressure reducing valve 2, gas hose 3, spray gun 4 and spray nozzle 6 is within 24 Kg or so. Such an apparatus can be freely moved by mounting the apparatus as a unit on the truck 5 having a simple structure as shown in FIG. 1, holding and inclining the grip pipe 53, and turning the left and right wheels 50. Furthermore, since this apparatus does not include a heater for heating, the power supply for the heater is unnecessary. Hence, for example, a plurality of wards of a hospital and the inside of a plurality of ambulances can be easily sterilized and disinfected by quickly moving the apparatus to the respective locations.

For sterilization and disinfection of the inside of an ambulance, a satisfactory result is obtained by 2 minutes spraying or so. With the use of a gas cylinder having a content capacity of 5 Kg, it is possible to sterilize and disinfect approximately 25 ambulances. In this sterilizing and disinfecting process, since spraying is stopped while moving the apparatus from one location to another, if the apparatus is designed to inject the carrier gas continuously for 15 minutes or more as described above, the process can be performed substantially continuously.

Besides, the gas cylinder 1 filled with compressed nitrogen gas is constructed using a high-strength resin such as Kevlar (product name) fiber reinforced resin so as to withstand the internal pressure of the nitrogen gas in a vaporized state. With the use of such a gas cylinder 1, it is possible to further decrease the total weight of the apparatus, and, for example, the user can use the apparatus while holding the gas cylinder 1 on his/her back.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A sterilizing and disinfecting apparatus for spraying a sterilizing and disinfecting chemical including alcohol into a target space, comprising:

a spray gun having an end nozzle;

a chemical container containing the chemical, attached to said spray gun;

a gas cylinder filled with a compressed carbon dioxide gas as a carrier gas;

a pressure reducing valve, attached near an outlet of said gas cylinder, for decompressing the gas discharged from the outlet to a pressure between 0.2-0.5 Mpa;

and a gas hose directly connected to the pressure reducing valve and the spray gun, wherein the spray gun sprays the chemical into the target space by a function of the carrier gas injected from the end nozzle, and wherein the spray gun, the end nozzle and the gas hose have dimensions that permit a feed rate of the gas that does not cause said carbon dioxide gas to freeze due to decompressing in the pressure reducing valve during continuous spray for at least 15 minutes.

2. The sterilizing and disinfecting apparatus according to claim 1, wherein the gas cylinder, pressure reducing valve and gas hose are mounted on a common truck shared by the spray gun and chemical container.

3. The sterilizing and disinfecting apparatus according to claim 2, wherein the chemical container is detachably attached to the spray gun.

4. The sterilizing and disinfecting apparatus according to claim 1, wherein the chemical container is detachably attached to the spray gun.

5. The sterilizing and disinfecting apparatus according to claim 1, wherein the chemical in the chemical container is a sterilizing and disinfecting chemical containing alcohol.

* * * * *